United States Patent
Sinofsky

(10) Patent No.: US 10,420,458 B2
(45) Date of Patent: Sep. 24, 2019

(54) LUMEN-LESS ILLUMINATION SYSTEM

(71) Applicant: Boston Scientific Scimed, Inc., Maple Grove, MN (US)

(72) Inventor: Edward L. Sinofsky, Dennis, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 381 days.

(21) Appl. No.: 14/699,682

(22) Filed: Apr. 29, 2015

(65) Prior Publication Data

US 2015/0374217 A1 Dec. 31, 2015

Related U.S. Application Data

(60) Provisional application No. 61/985,982, filed on Apr. 29, 2014.

(51) Int. Cl.
*A61B 1/06* (2006.01)
*A61B 1/005* (2006.01)
(Continued)

(52) U.S. Cl.
CPC ............ *A61B 1/0653* (2013.01); *A61B 1/005* (2013.01); *A61B 1/0011* (2013.01);
(Continued)

(58) Field of Classification Search
CPC . A61B 1/0653; A61B 1/00096; A61B 1/0011; A61B 1/005; A61B 1/043; A61B 1/045; A61B 1/0615; A61B 1/063
(Continued)

(56) References Cited

U.S. PATENT DOCUMENTS

| | | | |
|---|---|---|---|
| 3,269,387 A | 8/1966 | Wallace | |
| 3,637,518 A * | 1/1972 | Nada | C09K 11/0805 250/484.3 |

(Continued)

FOREIGN PATENT DOCUMENTS

| | | |
|---|---|---|
| CN | 101155545 A | 4/2008 |
| CN | 101765397 A | 6/2010 |

(Continued)

OTHER PUBLICATIONS

International Search Report and Written Opinion for corresponding PCT Application No. PCT/US2015/28225 dated Sep. 30, 2015 (16 pages).

(Continued)

*Primary Examiner* — Timothy J Neal
*Assistant Examiner* — Jae Woo
(74) *Attorney, Agent, or Firm* — Bookoff McAndrews, PLLC

(57) ABSTRACT

The present teachings relate to an endoscope (and methods of manufacturing the same) having an illumination system that utilizes small diameter fibers for delivering bright, high quality light to a target site. In accordance with one aspect, an endoscope is provided having a phosphor-loaded, light emitting distal tip that can be energized via optical radiation delivered to the light-emitting distal tip via a small-diameter optical fiber (e.g., less than about 100 μm in diameter) that extends through or along the length of the endoscope. The light-emitting distal tip can be energized by short wavelength laser light (e.g., radiation having wavelengths at 445 nm blue or 405 nm violet) coupled to the optical fiber's proximal end so as to deliver light of extremely high quality CRI (e.g., greater than 80, greater than 90, about 95).

30 Claims, 8 Drawing Sheets

(51) Int. Cl.
*F21K 2/00* (2006.01)
*C09K 11/77* (2006.01)
*A61B 1/00* (2006.01)
*A61B 1/04* (2006.01)
*A61B 1/045* (2006.01)
*A61B 1/07* (2006.01)
*A61B 1/018* (2006.01)

(52) U.S. Cl.
CPC .......... *A61B 1/00096* (2013.01); *A61B 1/043* (2013.01); *A61B 1/045* (2013.01); *A61B 1/063* (2013.01); *A61B 1/0615* (2013.01); *A61B 1/0669* (2013.01); *C09K 11/7715* (2013.01); *C09K 11/7728* (2013.01); *F21K 2/00* (2013.01); *A61B 1/018* (2013.01); *A61B 1/0676* (2013.01); *A61B 1/07* (2013.01)

(58) Field of Classification Search
USPC ....................................................... 600/178
See application file for complete search history.

(56) References Cited

U.S. PATENT DOCUMENTS

| | | | | |
|---|---|---|---|---|
| 5,025,778 | A | | 6/1991 | Silverstein et al. |
| 5,323,766 | A | * | 6/1994 | Uram ................. A61B 1/00165 600/108 |
| 5,601,525 | A | * | 2/1997 | Okada ................... A61B 1/002 359/435 |
| 6,389,205 | B1 | * | 5/2002 | Muckner ............ A61B 1/00117 362/574 |
| 6,554,765 | B1 | * | 4/2003 | Yarush ............... A61B 1/00039 348/73 |
| 7,980,745 | B2 | * | 7/2011 | Shanbaky ............ A61B 3/0008 362/231 |
| 8,024,027 | B2 | * | 9/2011 | Freeman .............. A61B 5/0075 600/473 |
| 8,251,897 | B2 | * | 8/2012 | Mizuyoshi ......... A61B 1/00096 600/178 |
| 8,626,273 | B2 | * | 1/2014 | Yamaguchi ........ A61B 1/00009 600/473 |
| 9,872,978 | B1 | * | 1/2018 | Zaborsky ................ A61L 2/08 |
| 9,895,460 | B1 | * | 2/2018 | Zaborsky ................ A61L 2/10 |
| 2003/0042493 | A1 | * | 3/2003 | Kazakevich ......... A61B 1/0607 257/98 |
| 2003/0050534 | A1 | * | 3/2003 | Kazakevich ......... A61B 1/0607 600/178 |
| 2004/0236275 | A1 | * | 11/2004 | Pruitt ..................... A61L 29/02 604/96.01 |
| 2006/0036164 | A1 | * | 2/2006 | Wilson ..................... A61B 5/06 600/424 |
| 2006/0069313 | A1 | * | 3/2006 | Couvillon, Jr. .......... A61B 5/06 600/179 |
| 2006/0198418 | A1 | * | 9/2006 | Hama ................. A61B 1/00096 372/108 |
| 2006/0235277 | A1 | | 10/2006 | Ohkubo et al. |
| 2006/0279950 | A1 | * | 12/2006 | Hama .................. A61B 1/0653 362/257 |
| 2007/0139950 | A1 | * | 6/2007 | Easley ..................... A61B 1/07 362/551 |
| 2007/0147033 | A1 | | 6/2007 | Ogawa et al. |
| 2008/0051632 | A1 | * | 2/2008 | Ito ........................ A61B 1/0607 600/114 |
| 2009/0039756 | A1 | * | 2/2009 | Yamamoto ......... A61B 1/00165 313/483 |
| 2009/0059359 | A1 | * | 3/2009 | Nahm ................ A61B 1/00165 359/368 |
| 2009/0147531 | A1 | | 6/2009 | Hsu et al. |
| 2011/0074942 | A1 | * | 3/2011 | Endo ...................... A61B 1/043 348/68 |
| 2012/0078052 | A1 | * | 3/2012 | Cheng .................. A61B 1/0676 600/139 |
| 2012/0101348 | A1 | * | 4/2012 | Yamaguchi ........ A61B 1/00009 600/317 |
| 2013/0155648 | A1 | * | 6/2013 | Morgenbrod ........ A61B 1/0653 362/84 |
| 2013/0314939 | A1 | * | 11/2013 | Ye ............................. F21K 9/52 362/551 |
| 2013/0331647 | A1 | | 12/2013 | Gingras |
| 2014/0357948 | A1 | | 12/2014 | Kikuchi et al. |

FOREIGN PATENT DOCUMENTS

| | | |
|---|---|---|
| CN | 102401914 A | 4/2012 |
| CN | 203017542 U | 6/2013 |
| CN | 203379097 U | 1/2014 |
| CN | 103987307 A | 8/2014 |
| EP | 1672755 A2 | 6/2006 |
| EP | 1867272 A1 | 12/2007 |
| JP | 2006-173498 | 6/2006 |
| JP | 2006-296498 | 11/2006 |
| JP | 2006-296656 | 11/2006 |
| JP | 2006-325691 | 12/2006 |
| JP | 2007-175433 | 7/2007 |
| JP | 2011072424 A | 4/2011 |
| WO | WO 2013/094569 A | 6/2013 |
| WO | WO 2013/168594 A1 | 11/2013 |

OTHER PUBLICATIONS

Supplemental Search Report in corresponding European Application No. 15785535.4 dated Dec. 4, 2017 (7 pages).
English translation of Office Action in corresponding Chinese Application No. 201580021816.5 dated Sep. 30, 2017 (11 pages).
Notification of third Chinese Office Action in corresponding Chinese Application No. 201580021816.5, dated Nov. 20, 2018 (16 pages—English translation included).
Notification of Second Chinese Office Action in corresponding Chinese Application No. 201580021816.5, dated May 8, 2018 (23 pages—English translation included).
Japanese Office Action in corresponding Japanese Application No. 2016-565158, dated Feb. 21, 2019 (3 pages).

\* cited by examiner

LUMEN-LESS ILLUMINATION SYSTEM

CROSS-REFERENCE TO RELATED APPLICATIONS

The present application claims benefit to Provisional Application 61/985,982, filed Apr. 29, 2014, which is herein incorporated by reference in its entirety.

FIELD

The teachings herein relate to the delivery of high brightness, high quality light to a remote location. For example, methods and apparatus (and their methods of manufacture) are disclosed herein for providing medical illumination through endoscopes to remotely view anatomies for diagnostic or therapeutic medical procedures.

INTRODUCTION

Endoscopes generally provide visualization of a target site within the human body and/or allow for the delivery of various tools (e.g., end effectors) to the target site. A typical working endoscope generally consists of three or more channels (e.g., lumens)—one lumen for the fiber that supplies illumination to the target site, one lumen that carries a visualization bundle or camera wires, and one lumen representing a working channel through which therapeutic instruments can be directed to the target site. Generally, the design of endoscopes represents tradeoffs in the size and relationship of the lumens and must take into account the implications of the lumens' effect on the flexibility of the endoscope as a whole.

Endoscopic light sources are typically based on incoherent light from high pressure lamps or high power white LEDs. Because the amount of light delivered to the target site is necessarily limited by the area of the fiber, the acceptance angle of the fiber, and the brightness of the light source, the low brightness of high power lamps and LEDs generally prevent the use of extremely small fibers. Accordingly, fibers having a diameter between about 400 µm to 1 mm or more are not uncommon. However, even with the use of larger (and correspondingly less flexible) optical fibers, the quantity of the light delivered to the target site is often inadequate. Though electronic gain of the system can be used to improve the quantity of light, this can also introduce artifacts to the image.

Furthermore, the quality of the light is also low for the high power lamps and LEDs typical of endoscopes. For example, present systems generally provide a low color rendering index (CRI), which compares the ability of the light to reveal the colors of an object relative to a perfect blackbody radiator (e.g., the sun), which exhibit no peaks or valleys in its spectrum. As a result, peaks and valleys of the typical endoscopic illumination light generally make the color of biological material look "off" or unnatural.

Accordingly, there remains a need for the delivery of high brightness, high quality light to a remote location, e.g., via an endoscope.

SUMMARY

In accordance with various aspects of the present teachings, certain embodiments of the applicant's teaching relate to an endoscope having an illumination system that utilizes small diameter fibers for delivering bright, high quality light to a target site. In accordance with various aspects, an endoscope is provided having a phosphor-loaded, light emitting distal tip that can be energized via optical radiation delivered to the light-emitting distal tip via a small-diameter optical fiber (e.g., less than about 100 µm in diameter) that extends through or along the length of the endoscope. By way of example, the endoscope can include a light-emitting distal tip comprising silicone being doped with a phosphor, and in some cases two, three, or possibly 4 phosphors (e.g., RGYB) loaded therein. As discussed in detail below, this phosphor-loaded distal section can form part of the distal tip, or can substantially comprise the entire tip, and can include one or more holes formed therethrough for the working channel and visualization bundle. In some aspects, this light-emitting distal tip can be energized by short wavelength laser light (e.g., radiation having wavelengths at 445 nm blue or 405 nm violet) generated by a semiconductor laser coupled to the optical fiber's proximal end so as to ultimately deliver light of extremely high quality CRI (e.g., greater than 80, greater than 90, about 95) from the light-emitting distal tip.

Though systems in accordance with the present teachings can enable the use of small-diameter fibers (e.g., fibers having a diameter less than about 100 µm) to illuminate an endoscope field-of-view and may satisfy a long felt need in the art, applicant has additionally found that such small fibers may make loading of the optical fiber within a dedicated internal channel extending along the length of the endoscope difficult. For example, it may be difficult to extrude an endoscope having an internal lumen diameter of between 0.05 mm to about 0.10 mm to accommodate the small diameter fiber and/or to load a small diameter fiber therein (e.g., the flexibility/floppiness of the small diameter fibers may make it difficult to load (e.g., push) the fibers into the lumen). Accordingly, in accordance with various aspects, rather than devoting an extruded lumen of the endoscope to receiving the optical fiber, the fiber and the light emitted therefrom can be delivered outside the endoscope extrusion (e.g., peripheral to the extruded endoscope), with the excitation light being directed laterally or radially into the phosphor-doped light-emitting tip by reflectance, for example. Alternatively, in some aspects, the distal tip of the optical fiber can be embedded in the phosphor-loaded distal tip of the endoscope for providing the excitation light to be delivered radially or distally. In some aspects, the optical fiber's proximal portion (e.g., proximal to the light-emitting tip) can be laminated onto the surface (e.g., the circumferential surface) of the endoscope with adhesive, melted into the surface with heat, or alternatively, not proximally attached to the scope at all.

It will be appreciated in light of the present teachings that the absence of a specific illumination lumen in the endoscope extrusion can enable a larger working channel to be utilized, for example, to ease the passage of therapeutic instruments or reduce the overall diameter of the device so as to reduce patient trauma. In accordance with various aspects, the present teachings can enable the use of small diameter optical fibers less than 100 µm in diameter (e.g., about 50 µm). Moreover, a more flexible device can also result due to the decreased diameter of the endoscope, as well as the decreased bending moment of the significantly smaller fiber.

It will also be appreciated in light of the present teachings that the size of the imaging bundle can be reduced due to the improved quantity and/or quality of light that illuminates the target site. That is, in the case of an increased quantity and/or quality of light delivered to the target site, a smaller and/or less-expensive imaging/visualization bundle can advantageously be utilized, while nonetheless improving the quality of images of the target site. By way of non-limiting example, in some aspects, 150 mW of violet excitation light (e.g., at 405 nm) can be delivered through a small optical fiber to the phosphor-doped light-emitting tip to produce more than 50 lumens of white light (sufficient to illuminate a body cavity many centimeters in diameter), with efficiencies as high as 400 lumens/watt. For comparison, this is as much white light as can be produced by a mid-sized LED, which cannot be fiber coupled through a fiber having a diameter less than 100 µm.

In accordance with various aspects of the present teachings, certain embodiments of the applicant's teaching relate to an endoscopic system comprising an endoscope that extends from a proximal end configured to be disposed external to a patient to a distal end configured to be disposed adjacent a target site within the patient. The endoscope (e.g., an extruded endoscope) can have a visualization channel configured to receive a visualization bundle for imaging the target site. The system can also include a radiation source configured to generate excitation radiation and an optical fiber configured to receive the excitation radiation at a proximal end thereof and transmit the excitation radiation to its distal end. One or more phosphors disposed at the distal end of the endoscope and surrounding said visualization channel can be configured to receive the excitation radiation output from the distal end of the optical fiber and emit illuminating radiation toward the target site in response to receiving the excitation radiation. In some aspects, the optical fiber can have a diameter of less than about 100 µm.

In some aspects, the optical fiber extends from a proximal end to a distal end along a longitudinal axis, and the one or more phosphors are disposed off-axis. In some aspects, for example, the one or more phosphors surround a perimeter of the optical fiber. Alternatively or additionally, the one or more phosphors can be dispersed throughout a polymer that substantially encompasses the distal end of the endoscope.

In some aspects, the optical fiber is disposed along the endoscope periphery. For example, the endoscope can lack an internal lumen for receiving the optical fiber. In various aspects, the endoscope can also include a working channel through which one or more instruments can be delivered to the target site. For example, only two lumens can extend through an interior of the endoscope, the lumens comprising the working channel and the visualization channel.

In some aspects, the illuminating radiation can exhibit a range of wavelengths. For example, the illuminating radiation can substantially encompass the visible spectrum. As discussed herein, the one or more phosphors can be configured to generate illuminating radiation exhibiting a CRI greater than about 70, greater than about 80, greater than about 90, or greater than about 95.

In accordance with various aspects of the present teachings, certain embodiments of the applicant's teaching relate to an endoscopic system comprising an endoscope extending from a proximal end configured to be disposed external to a patient to a distal end configured to be disposed adjacent a target site within the patient, an optical fiber for delivering excitation light to the distal end of the endoscope, wherein said distal end comprises a polymeric tip having one or more phosphors disposed therein for emitting light from the distal tip toward the target site after being stimulated by the excitation light.

In some aspects, the endoscope can include an internal lumen through which a visualization bundle is configured to extend and a working channel though which one or more one or more instruments can be delivered to the target site. In related aspects, the internal lumen and the working channel extend through the polymeric tip, wherein said one or more phosphors are dispersed in said polymer in a space between the internal lumen and the working channel and/or surrounding the internal lumen and the working channel.

In accordance with various aspects, the endoscope can be formed through an extrusion process such that the extruded endoscope comprises only two channels extending along the length thereof. For example, the optical fiber can be disposed external to the extruded endoscope.

As noted above, excitation light can be delivered to the polymeric tip so as to cause the phosphors disposed therein to emit illumination light. By way of example, the optical fiber can terminate in a distal end disposed within or adjacent the polymeric tip, and the excitation light can be directed radially from a terminal distal end of the optical fiber into the polymeric tip. The excitation light can be generated by a variety of sources and can be tuned to maximize emission of illuminating light by the one or more phosphors. For example, the excitation light can be in the blue portion of the spectrum (e.g., substantially coherent light having a wavelength of about 445 nm). Alternatively, in some aspects, the excitation light can be in the violet portion of the spectrum (e.g., substantially coherent light having a wavelength of about 405 nm).

In response to the excitation light received thereby, the distal tip can be configured to emit substantially white light. For example, the light emitted from the distal tip exhibits a CRI greater than about 70, greater than about 80 (e.g., the polymeric tip can include a green and a red phosphor dispersed within the polymer), greater than about 90 (e.g., with three or more phosphors), and greater than about 95 (e.g., with fours phosphors and excitation light in the violet portion of the spectrum).

In some aspects, the optical fiber can have a diameter of less than about 100 µm. Thus, for example, flexibility of the endoscopic system can be remain substantially unchanged relative to an endoscopic system lacking the optical fiber. Moreover, in some aspects, the optical fiber can have a cross-sectional area less than about 0.25% of the endoscope, thus enabling for the provision of a larger working channel, for example.

In some aspects, the one or more phosphors can be encapsulated within an undoped polymer to prevent contact of the one or more phosphors with the patient. For example, in some aspects, the phosphor-doped polymer can be encapsulated within an undoped polymer. Although many phosphors for use in the present teachings are non-toxic, it may nonetheless be advantageous to encapsulate phosphors to prevent contact of Eu- and Ce-dopants with a patient.

In some aspects, the endoscopic system can also include a detector configured to receive light emitted from the one or more phosphors at the distal tip and back-transmitted through the optical fiber toward the proximal end. For example, the detector can be disposed at the proximal end of the optical fiber. A controller can also be provided that is responsive to the detector, the controller being configured to prevent transmission of excitation light through the optical fiber if back-transmitted light is not detected. For example, the controller can be configured to deactivate the radiation source that generates the excitation light if back-transmitted light is not detected.

Methods for manufacturing the exemplary endoscopic systems described herein are also provided. In accordance with various aspects, the method of manufacturing an endoscopic system can include curing a polymer containing at least one of phosphors and scattering agents at the distal end of an extruded endoscope (e.g., an extruded endoscope comprising a working channel and a visualization channel). In some aspects, the method can also include extruding the endoscope prior to curing the polymer containing the phosphors or scattering agents at the distal end.

In some aspects, the method can also include coupling an optical fiber to an external surface of the extruded endoscope. For example, the optical fiber can be adhered onto the surface (e.g., with adhesive) or melted into the surface with heat.

In some aspects, the method can include obtaining an emission spectrum of the light emitted from the distal tip while mixing said two or more phosphors within the uncured polymer, for example, so as to tune the light to be generated at the distal end of the endoscope.

In some aspects, methods for encapsulating the phosphor-doped polymer within an undoped polymer are also provided. Although many phosphors for use in the present teachings are non-toxic, it may be nonetheless be advantageous to encapsulate the phosphor to prevent contact of the Eu- and Ce-dopants with the patient.

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way.

DETAILED DESCRIPTION

Figure 1:
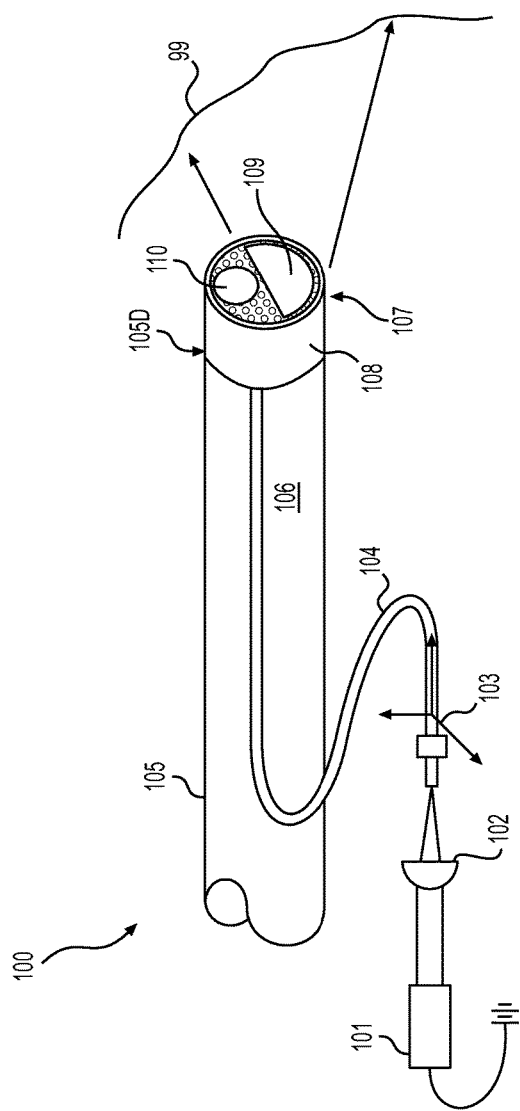
FIG. 1, in schematic diagram, depicts an exemplary endoscope having an illumination system in accordance with various aspects of the present teachings.

It will be appreciated that for clarity, the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicant's teachings in any manner.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $\frac{1}{10}$ of the stated values, e.g., ±10%. For instance, a concentration value of about 30% can mean a concentration between 27% and 33%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

Methods and systems for providing high brightness, high quality light to a remote location are provided herein. In accordance with various aspects of the applicant's teachings, the methods and systems (and their methods of manufacture) can provide improved illumination for endoscopic therapeutic or diagnostic medical procedures. Although various aspects of the invention are discussed herein with reference to endoscopes, it will be appreciated that the present teachings can have broader applicability, for example, in instances where remote illumination in a difficult-to-reach space is desirable. In some embodiments, an endoscope is provided having a phosphor-loaded, light-emitting distal tip that can be energized via optical radiation delivered to the light-emitting distal tip via a small-diameter optical fiber (e.g., less than about 100 µm in diameter) that extends through or along the length of the endoscope. In some aspects, this light-emitting distal tip can be energized by short wavelength laser light (e.g., radiation having wavelengths at 445 nm blue or 405 nm violet) generated by a semiconductor laser coupled to the optical fiber's proximal end so as to deliver light of extremely high quality CRI (e.g., greater than 80, greater than 90, about 95).

The term "endoscope" as used herein is intended to encompass instruments for visually examining the interior of a bodily canal or a hollow organ, such as the stomach, bladder, or colon. The term "phosphor" as used herein generally denotes a substance that exhibits luminescence, typically in response to incident light.

With reference now to FIG. 1, an exemplary endoscopic system 100 configured to deliver bright, high-quality light to a target site (e.g., visualization target 99) in accordance with various aspects of applicant's teachings is illustrated schematically. As will be appreciated by a person skilled in the art, the system 100 represents only one possible configuration in accordance with various aspects of the systems, devices, and methods described herein. As shown in FIG. 1, the exemplary system 100 generally comprises an endoscope 105 configured to extend from a proximal end (not shown) disposed external the patient to a distal end 105d that can be disposed near a visualization target 99 (e.g., internal to a patient, within a body cavity). It will be appreciated by those skilled in the art that the distal end 105d of the endoscope 105 can be delivered, for example, through a natural passageway (e.g., esophagus) or an incision (e.g., through the skin). As discussed in detail below, the exemplary endoscopic system 100 additionally includes an illumination system for illuminating the target site 99 that includes an optical fiber for delivering radiation to the distal end 105d of the endoscope 105.

Illumination systems in accordance with the present teachings can have a variety of configurations, but can generally include a radiation source for generating excitation radiation (also referred to herein as pumping radiation) to one or more phosphors that are excited thereby, and which in turn, emit light that is directed at the visualization target 99. For example, in the exemplary embodiment depicted in FIG. 1, the exemplary illumination system includes a radiation source 101 (e.g., energized by a power source) that generates light that can be coupled into a fiber optic 104. As discussed in detail below, in some embodiments the optical fiber 104 can exhibit a diameter less than about 100 µm (e.g., about 50 µm).

It will be appreciated in light of the present teachings that the radiation delivered to the optical fiber 104 can be generated by a variety of light sources (e.g., a semiconductor laser, laser, diodes, solid state lasers) that can produce light effective to excite one or more phosphors and/or be scattered by scattering agents, as discussed otherwise herein.

Moreover, it will be appreciated that the excitation light can be coupled into the fiber optic 104 with a variety of mechanisms, for example, using one or more optical elements. As shown in FIG. 1, for example, the exemplary endoscopic system 100 includes a radiation source 101 that can include a collimating lens through which the emitted radiation passes. This light can be focused, for example, with a plano-convex focusing lens 102, for focusing the received light into the optical fiber 104. It will be appreciated that the focusing lens 104 can be coated with an antireflection coating to increase its transmission efficiency. In various aspects, the focal length of this lens 102 can be chosen so as to focus the beam at the optical fiber 104 with a spot size of between about 20 µm to about 50 µm, which can enable the use of the small-diameter fibers as otherwise discussed herein. The fiber 104, which can be mounted and polished in a connector positioned at the focus of the beam by fiber positioner 103. In some aspects, transmission percentages of 85-90% can be achievable.

As shown in FIG. 1, the light from the radiation source that is coupled into the optical fiber 104 can be delivered to the distal end 105d of the endoscope 105 so as to excite the one or more phosphors disposed at the distal end 105d. By way of example, in an endoscope 105 formed by an extrusion process having an outer circumferential surface 106 defined by the extruded polymer, the optical fiber 104 can be coupled to the circumference of the extrusion. Thus, whereas known endoscopes generally include an internal lumen through which an optical fiber is threaded after extrusion of the endoscope, the exemplary endoscope 105 need not include a dedicated lumen for the optical fiber 104.

Rather, the low-profile fiber 104 can be coupled to the outside the endoscope extrusion (e.g., peripheral to the extruded endoscope). For example, the proximal portion of the optical fiber 104 (e.g., the portion proximal to the distal end 105d) can be laminated onto the circumferential surface of the endoscope extrusion 106 with an adhesive, melted into the surface with heat. Alternatively, the optical fiber 104 can be disposed within a channel formed in the outer surface of the extrusion 106, and retained therein by an interference fit, for example. In some aspects, the fiber 104 need not be proximally attached to the scope at all. The fiber can bifurcate off of the extrusion at any convenient location along it's length and be led to the laser independently.

As shown in FIG. 1, the exemplary endoscopic system 100 terminates in a light-emitting distal tip 107 associated with, for example, one or more phosphors that are configured to be excited upon receiving the light transmitted by the optical fiber 104 and/or scattering agents that can scatter the light transmitted by the optical fiber 104. In the depicted exemplary embodiment of FIG. 1, the light-emitting distal tip 107 can comprise a polymer (e.g., a high durometer silicone, a biocompatible polymer, a thermosetting polymer, a thermoplastic polymer, etc.) having one or more phosphors dispersed therein and surrounded by a reflective band 108 (e.g., a metal or metallized surface, a reflective polymer such as a white heatshrink tubing) for maximizing the transmission of light generated by the phosphor(s) toward the visualization target 99. The output end of the fiber optic 104, which can terminate inside the reflective band 108, emits its light into the distal tip 107 such that the light bounces around and/or is scattered within the polymer, and in some aspects, stimulates emission from the phosphors dispersed therein. As shown in FIG. 1, for example, the phosphor(s) and/or scattering agent(s) can be dispersed throughout the polymer that encompasses substantially the entire cross-sectional area (e.g., the entire distal face) of the endoscope 105. In some aspects, for example, the phosphor(s) and/or scattering agent(s) can be dispersed such that they substantially surround the visualization lumen 110 and/or working channel 109 extending through the polymer, as discussed in detail below. For example, the phosphor(s) and/or scattering agent(s) can be dispersed in the polymer off the major longitudinal axis of the optical fiber (e.g., surrounding the perimeter of the optical fiber, such that light can be transmitted laterally or radially to excite the phosphor(s)). In accordance with some aspects, the distal face of the extruded endoscope 105 can also be reflective (like reflective band 108) such that light emitted by the excited phosphors and/or scattered by the scattering agents in the backwards direction (e.g., proximally) or laterally (e.g., toward the reflective band 108) can be redirected toward the visualization target 99.

Figure 2A:
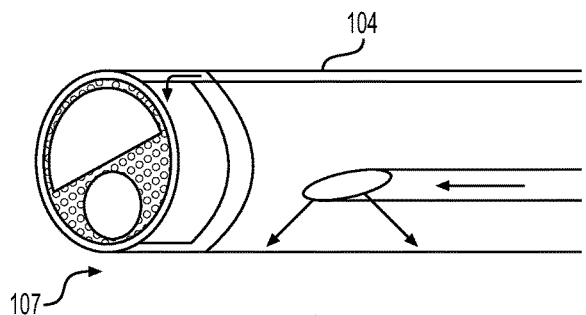
FIG. 2A, in schematic diagram, depicts an exemplary light-emitting distal tip of FIG. 1 in accordance with various aspects of the present teachings.

The pumping or excitation light transmitted by the optical fiber 104 along the length of the endoscope 105 can be coupled into the phosphor-doped polymer within the reflective band 108 of the light emitting tip 107 in a variety of manners such that the phosphor is excited and glows so as to generate and/or emit white light at the tip of the endoscope 105 itself. For example, with reference now to FIG. 2A, the excitation light can be directed laterally into the phosphor-doped light-emitting tip 107 by a reflection of the light at the output end of the optical fiber 104. For example, as shown in FIG. 2A, the distal-most end of the optical fiber 104 can include a chisel-tip by polishing (e.g., for glass fibers) or cutting (for plastic fibers) the fiber such that the light undergoes total internal reflection on the surface such that the light bends (e.g., laterally, at a right angle) and is emitted through the side of the optical fiber). Though reflection from the reflective band 108 should be effective to deliver the light to the phosphors within the polymer regardless of the rotation of the chisel tip, it may be preferable to dispose the chisel tip such that light is reflected thereby toward the center of the doped polymer. To maximize total internal reflection, the fiber is preferably placed outside the phosphor doped polymer to ensure that the light transmitted along the length of the fiber 104 is incident on the chisel tip at an angle greater than the critical angle (which depends on the indices of refraction).

Figure 2B:
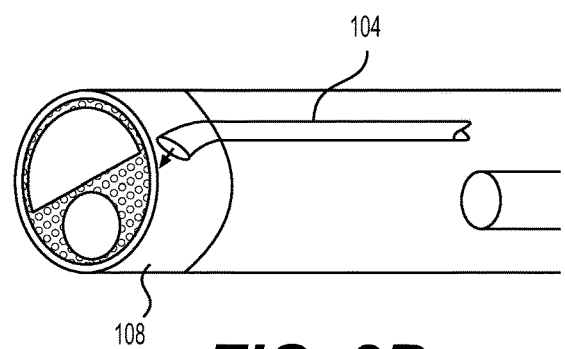
FIG. 2B, in schematic diagram, depicts another exemplary light-emitting distal tip in accordance with various aspects of the present teachings.

With reference now to FIG. 2B, another exemplary mechanism for coupling the pumping or excitation light from the optical fiber 104 into the phosphor-doped polymer of the light emitting tip 107 is depicted. As shown in FIG. 2B, a square polished (glass fiber) or cut (plastic fiber) distal top of the optical fiber 104 can be embedded (e.g., off axis) in the polymer or directed into the polymer doped with phosphors and/or scattering agents. As such, light from the end of the fiber 104 can be scattered by either the phosphor particles and/or scattering particles (and in some aspect, initiate emissions from the phosphors) for reflection off of the boundaries of the polymer and reflective band 108 to create a uniform "glowball" at the distal tip of the endoscope.

Figure 2C:
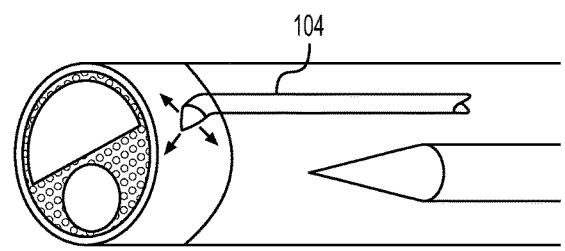
FIG. 2C, in schematic diagram, depicts another exemplary light-emitting distal tip in accordance with various aspects of the present teachings.

With reference now to FIG. 2C, another exemplary distal tip of the optical fiber 104 is depicted in which the optical fiber 104 exhibits a drastic pull down (or taper) that forces the fiber 104 to emit radially over this segment. This draw down taper can be manufactured, for example, in a fusion splicer for glass fibers and with a simple heat source for plastic fibers. In both cases, the region of a few millimeters is heated and simultaneously pulled as the material melts. The draw down process results in a terminated cone that emits light to the side, rather than out the end as in FIG. 2B. In some aspects, the draw down taper tip can be disposed within the phosphor-dope polymer itself.

Figure 3A:
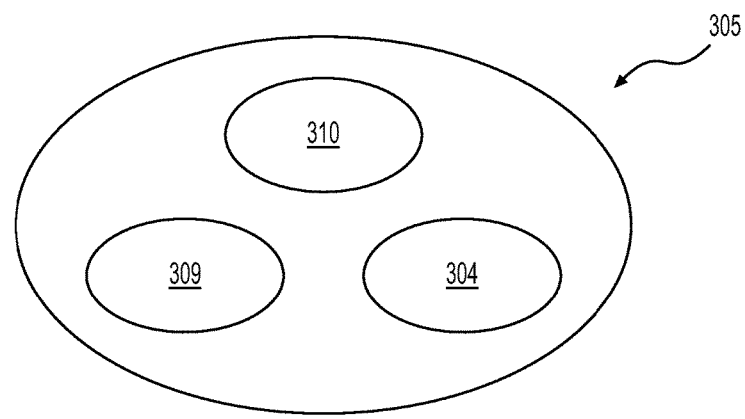
FIGS. 3A and 3B, in schematic diagram, depict the comparative cross sections of a known endoscope having three lumens (illumination, visualization, and working channel) and the exemplary endoscope of FIG. 1.
Figure 3B:
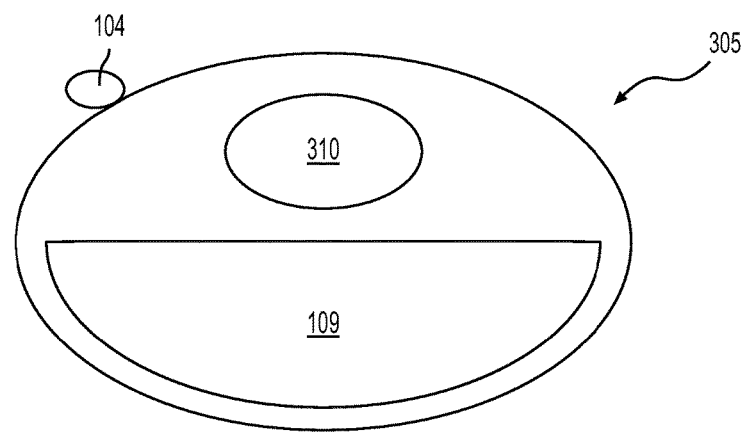

As will be appreciated in light of the present teachings, endoscopic systems that provide for a working channel (and a lumen for a visualization bundle) need not also include a dedicated lumen for illumination such that the dimensions of the working channel can be increased, for example, to ease access for tools therethrough, or the overall diameter of the endoscope 105 can be reduced so as to reduce potential for patient trauma. That is, with reference again to FIG. 1, the exemplary endoscope 105 includes a working channel and a visualization channel, but no channel for illumination or the optical fiber 104 as in known endoscopes. With reference now to FIGS. 3A and 3B, the comparative cross sections of a traditional endoscope 305 having three lumens (illumination 304, working channel 309, and visualization lumen 310) (FIG. 3A) and the exemplary endoscope 105 of FIG. 1 having two lumens (a working channel 109 and visualization lumen 110, with the optical fiber 104 being disposed along the external circumferential surface) is depicted. By way of example, whereas the illumination channel 304 generally requires between about 2-10% of the cross-sectional area of prior art endoscopes (e.g., about 2-10% of an exemplary endoscope having a 3 mm diameter), endoscopic systems in accordance with the present teachings can enable the optical fiber 104 to account for a significantly-reduced portion of the cross-sectional area. By way of example, for a 3 mm endoscope 105 manufactured in accordance with various aspects of the present teachings, the optical fiber can account for less than 0.25% of the cross-sectional area of the endoscope 105, a reduction of more than an order of magnitude relative to known devices. As will be appreciated by a person skilled in the art in light of the present teachings, when the illumination channel 304 that typically houses the relatively-large diameter optical fiber utilized in prior devices is eliminated from the extrusion, the size of the working channel 109 can be increased, thereby allowing a wider range of working instruments to be used or easier positioning of commonly-utilized working instruments. It will also be appreciated that the overall diameter of the endoscope 105 can alternatively be reduced, for example, while maintaining the same size working channel 109 and visualization channel 110 as the endoscope 105 need no longer provide for an interior extruded, illumination channel 304, which can provide for more robust systems.

Moreover as discussed otherwise herein, in light of the improved quality and/or increased quantity of light delivered to the target site, it will be appreciated that the size of the imaging bundle, or camera chip, can also be reduced. That is, in the case of an increased quantity and/or quality of light delivered to the target site, a smaller and/or less-expensive imaging/visualization bundle or detector/camera chip can advantageously be utilized, while nonetheless improving the quality of the images of the target site.

With reference again to FIG. 1, one or more phosphors that are configured to be excited upon receiving the light transmitted by the optical fiber 104 can be contained within the light-emitting distal tip 107. The output end of the fiber optic 104, which can terminate inside the reflective band 108, emits its light into the distal tip 107 and stimulates emission from the phosphors dispersed therein so as to generate and/or emit white light from the distal end of the endoscope 105. It will be appreciated that a variety of phosphors known in the art and modified in accordance with the present teaching can be utilized to generate light at the distal end of the endoscope for illuminating the target site. Exemplary phosphors include $Ce^{3+}$:YAG, $Ce^{3+}$:LuAg, $Ce^{3+}$:Oxynitride, silicate-based phosphors (e.g., $Eu^{2+}$:$Sr_3SiO_5$), nitride-based phosphors (e.g., $Eu^{2+}$:$Sr_2Si_5N_8$), $Eu^{2+}$:$Ba_2MgSi_2O_7$, $Eu^{2+}$:$Ba_3MgSi_2O_8$, and $Eu^{2+}$:$LiSrPO_4$, all by way of non-limiting example. In some aspects, by way of non-limiting example, 150 mW of violet excitation light (e.g., at 405 nm) delivered through a small optical fiber to the light-emitting tip can produce more than 50 lumens of white light (sufficient to illuminate a body cavity many centimeters in diameter), with efficiencies as high as 400 lumens/watt. By way of comparison, this is as much white light as can be produced by a mid-sized LED, which cannot be coupled into an optical fiber having a diameter less than 100 μm.

As noted above, the excitation or pumping radiation can be generated by a variety of light sources, e.g., one or more pumping light sources producing wavelengths configured to stimulate emissions from one or more phosphors. For example, with reference now to FIGS. 4A and 4B, exemplary comparative spectra of the light emitted from one or more phosphors contained within a light-emitting distal tip of an endoscope of FIG. 1 when stimulated by blue laser light having a wavelength of about 445 nm are depicted.

Figure 4A:
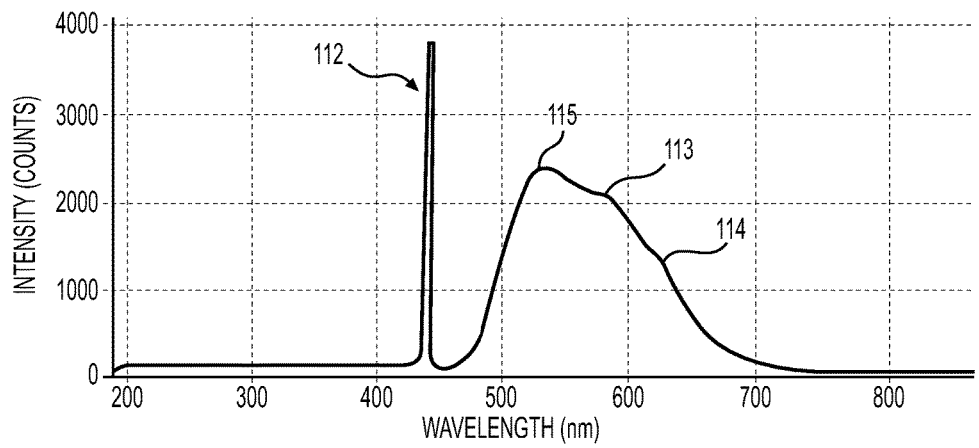
FIGS. 4A and 4B depict exemplary spectra generated by one or more phosphors excited by 445 nm blue pump light in accordance with various aspects of the present teachings.

As shown in FIG. 4A, an exemplary spectrum exhibiting a CRI of about 80 is depicted. The exemplary spectrum is generated by a 445 nm blue laser (peak 112) stimulating emission from three phosphors: one in the green portion of the spectrum (peak 115), one in the yellow (peak 113), and one in the red (peak 114). Exemplary green and yellow phosphors include $Ce^{3+}$:YAG, $Ce^{3+}$:LuAg, or $Ce^{3+}$:Oxynitride. Silicate-based phosphors such as $Eu^{2+}$:$Sr_3SiO_5$ can also be used to generate light in the yellow region of the spectrum. Exemplary red phosphors, which are typically nitride-based, include $Eu^{2+}$:$Sr_2Si_5N_8$.

While the enhanced red and green emissions of FIG. 4A result in an improved CRI relative to the quality of light emitted by a single yellow phosphor in accordance with aspects of the present teachings and the light generated by white LEDs in most non-critical applications (e.g., about 70 CRI, which can appear harsh as it doesn't include substantial green or red wavelengths desired for some high quality light applications), the blue/green portion of the spectrum may still be improved as this region can be important in distinguishing anatomies having vascularization. For example, with reference now to FIG. 4B, an exemplary spectrum exhibiting a CRI of about 90 is depicted in which a cyan phosphor that emits light in the blue/green portion of the spectrum (peak 116) is added to the three phosphors utilized to produce the spectrum of FIG. 4A. An exemplary cyan phosphor is $Eu^{2+}$ in $Ba_2MgSi_2O_7$, by way of non-limiting example.

Figure 4B:
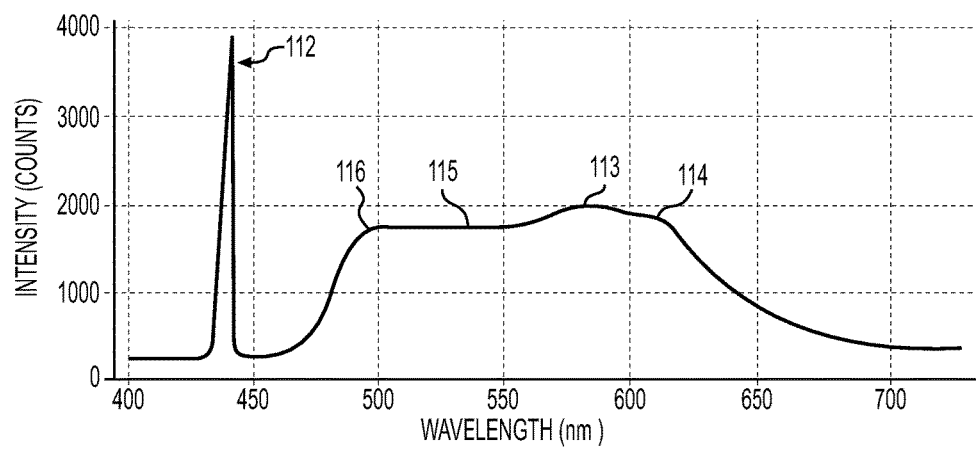

As shown in FIG. 4B, the addition of the cyan phosphor (peak 116) extends the wavelength range (e.g., shortens the shortest wavelength of emitted light) to the edge of the blue-green. In such embodiments, white light with a CRI of up to 90 can be emitted from the distal tip, though the speckle resulting from the blue pump light may nonetheless be observed. That is, because the excitation light of 445 nm is visible to the user, some of the coherent excitation light output by the optical fiber 104 may be observed directly at the visualization site. For example, the coherent, directional pump light can produce a speckle pattern within the lambertian diffusion pattern of the fluorescent light emitted by the phosphors, which may interfere with visualization and/or be annoying to the viewer. Moreover, a dip in the intensity of blue light of wavelengths distinct from the excitation light is also indicated in FIG. 4B. Indeed, because of the narrower emission region of the pump laser relative to an LED, for example, the deficiencies in the blue region may be more noticeable.

Figure 5:
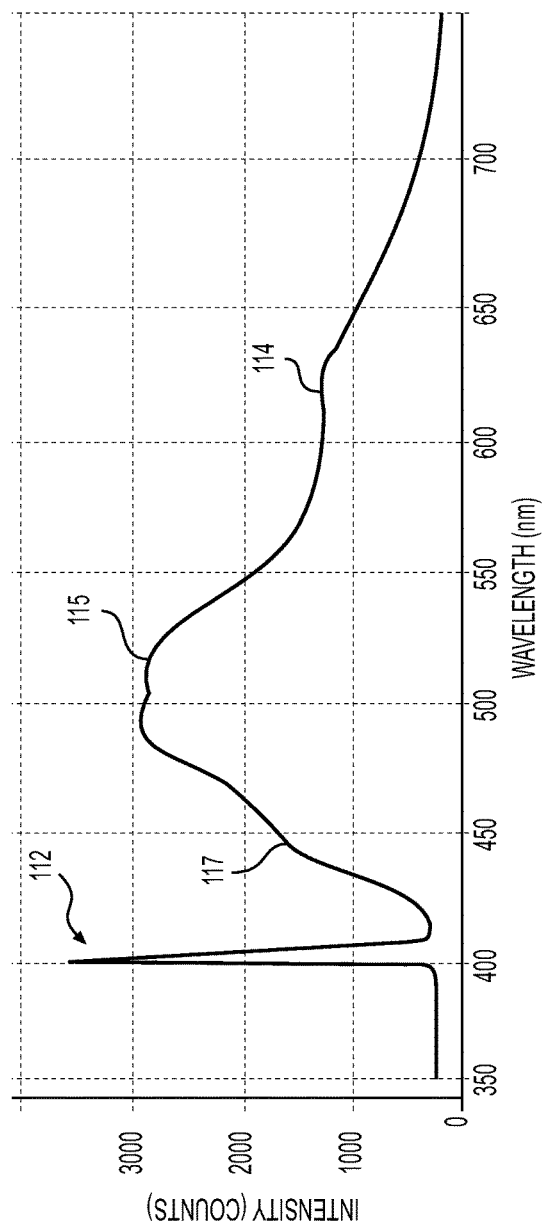
FIG. 5 depicts an exemplary spectrum generated by multiple phosphors excited by a 405 nm violet pump light in accordance with various aspects of the present teachings.

Though this increased range of FIG. 4B may be sufficient in some applications, deficiencies in the blue region may nonetheless be observed. Because there exists many biological pigments in the blue/green portion of the spectrum, in some aspects it is preferable to utilize shorter wavelength violet light (e.g., from a solid state laser emitting light at about 405 nm) to excite the phosphors within the light-emitting distal tip. Commercially-available lasers emitting in this wavelength (e.g., Blu-ray lasers) can be relatively inexpensive and highly-focusable such that high transmission coupling to the exemplary 50-100 μm diameter fibers can be achieved. As shown in FIG. 5, for example, by utilizing violet excitation light (peak 112) and three phosphors (e.g., blue $Eu^{2+}$ Phosphates and Silicates, green/yellow Eu2+ Silicates, YAG, LuAg, or Oxynitrides, and red $Eu^{2+}$ Nitrides, the emitted light can include blue (peak 117), green (peak 115) and red (peak 114) incoherent color bands exhibiting a CRI of 95 or greater, which can provide the viewing physician the same colors as incandescent or natural sunlight. The spectrum of the emitted light is made up of a smooth constant light output from about 450 nm to about 650 nm, or the entire visible spectrum. Moreover, the 405 nm pump light is generally outside of the human eye sensitivity such that speckle can be reduced or eliminated. Exemplary blue phosphors that are pumped at 405 nm include $Eu^{2+}:Ba_3MgSi_2O_8$ having an emission peak at 440 nm and $Eu^{2+}:LiSrPO_4$, by way of non-limiting example. It will be appreciated that one or more additional phosphors (e.g., cyan or yellow) can be added and that not each of blue, green, or red is required. Indeed, it will be appreciated in light of the present teachings that adjustment of the relative amounts of the phosphors can create spectra that are near perfect compared to the light from the sun or incandescent bulbs. CRIs of 95 or higher can thus be obtained, which looks exquisite to the human eye.

Figure 6:
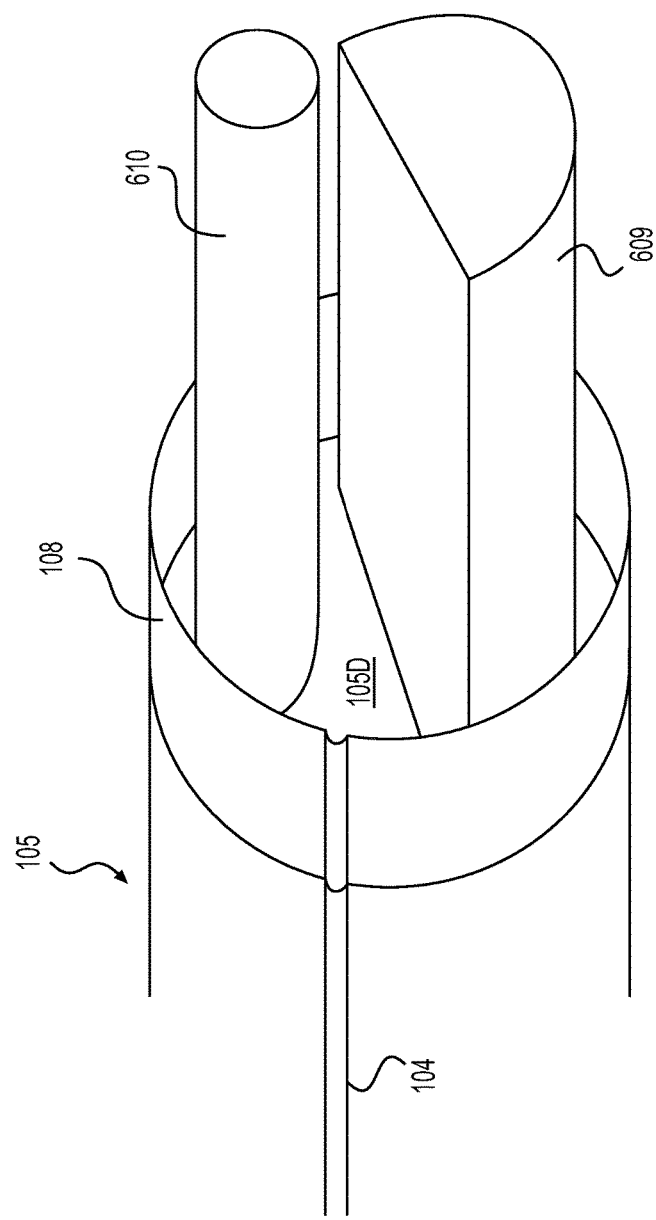
FIG. 6 depicts an exemplary technique for manufacturing the exemplary light-emitting distal tip of FIG. 1.

With reference now to FIG. 6, an exemplary technique for manufacturing an endoscope having a light-emitting distal tip is depicted. As shown in FIG. 5, an endoscope 105 can be provided. It will be appreciated that the endoscope 105 can be produced using a variety of processes and materials in accordance with known techniques. By way of example, the endoscope 105 can be formed through an extrusion process such that the endoscope 105 has one or more lumens extending therethrough. In various aspects, the extruded material of the endoscope 105 can be highly reflective. For example, by loading the polymer with Barium prior to extrusion, the extrusion process may result in an endoscope material in which the bulk material appears white and highly reflective. The distal end 105d of the endoscope 105 can be cut perpendicularly, and the optical fiber can be coupled to external surface of the endoscope extrusion, as otherwise discussed herein.

Next, a mold can be placed around the terminal end of the optical fiber 104 and the distal end 105d of the endoscope (e.g., extending distally beyond the distal end 105d by several millimeters), thereby defining a volume into which a polymer is to be cast. Mandrels can be placed in the lumens of the endoscope formed during the extrusion process for preventing polymer from flowing into the lumens. For example, mandrel 609 can be placed in the working lumen 109 and mandrel 610 can be placed in the visualization or camera lumen 110.

With the mandrels in place and the terminal end of the optical fiber 104 disposed in a desired orientation (e.g., as in one of FIGS. 2A-C), a polymer can then be cast into the volume defined by the mold. As noted above, the polymer can comprise a variety of materials (e.g., a high durometer silicone, a biocompatible polymer, a thermosetting polymer, a thermoplastic polymer, etc.) that can be mixed with a desired concentration of scattering particles and/or phosphors prior to curing thereof. In some aspects, live spectral measurements of the polymer during mixing of the phosphors can be taken (e.g., using the intended pumping light wavelength to stimulate the polymer) such that the desired concentration and/or spectral balance of the phosphor(s) can be obtained. The polymer can then be set and the mold and mandrels 609, 610 removed. Alternatively, in some aspects, the reflective band 108 as discussed above in FIG. 1 could serve as the mold and thus, remain in place following the setting of the polymer.

Figure 7:
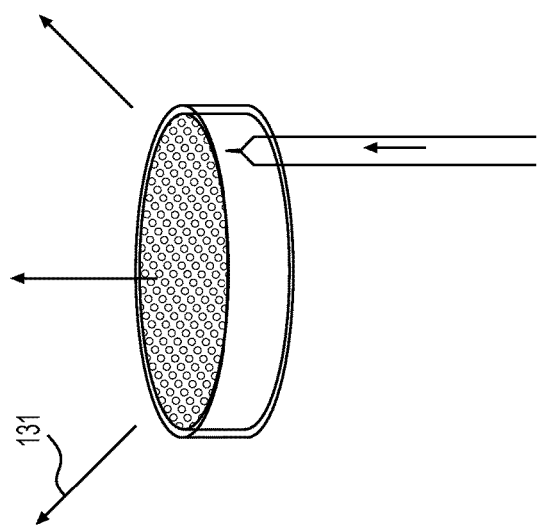
FIG. 7, in schematic diagram, depicts another exemplary endoscope having a light-emitting distal tip in accordance with various aspects of the present teaching.
Figure 7:
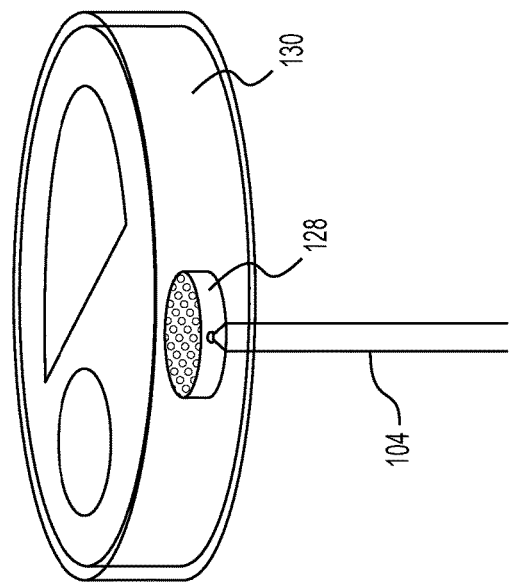

Alternatively, with reference now to FIG. 7, rather than the phosphor(s) being dispersed throughout the entirety of the polymer at the distal end, the phosphor(s) can be wholly encapsulated within the distal tip to avoid contact with the body, for example. By way of example, a volume (e.g., disk 128) of polymer doped with phosphor can be pre-set and disposed within the volume of the mold, with the output end of the optical fiber 104 being directed thereat. A biocompatible, transparent, undoped polymer, for example, can then be cast over the disk 128 to encapsulate the phosphor within the distal tip, while shielding the body from phosphor contact. As depicted in FIG. 7, the excitation light from the optical fiber 104 can cause the phosphors within the disk 128 to emit light 131, which can then be transmitted through the clear encapsulant 130 to the visualization site.

Figure 8:
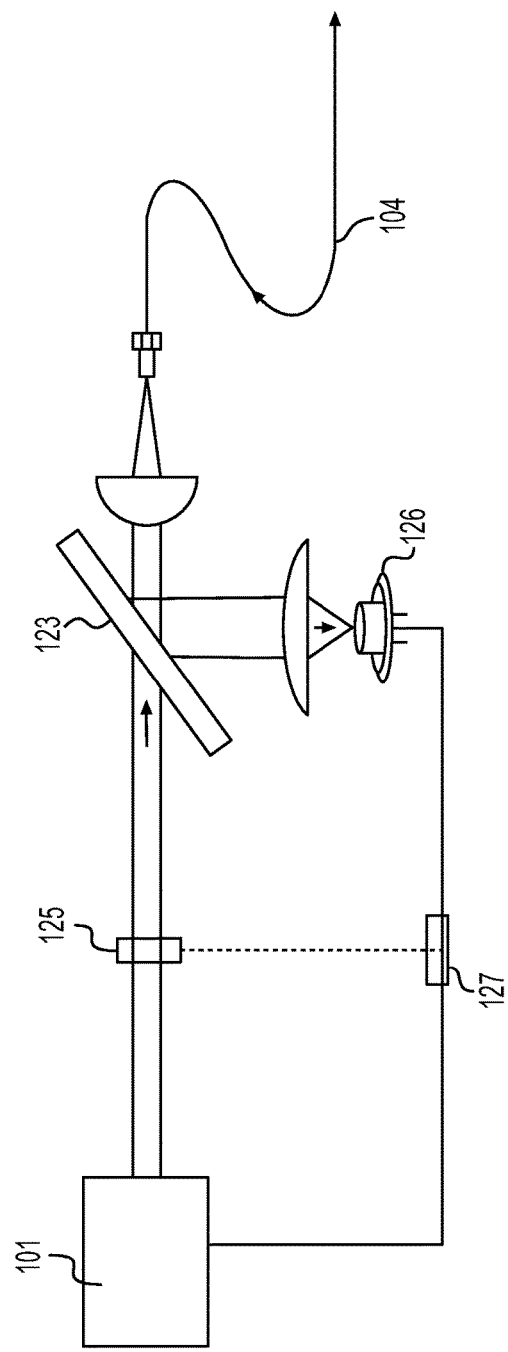
FIG. 8, in schematic diagram, depicts an exemplary illumination system having a safety system in accordance with various aspects of the present teachings.

In various aspects, the exemplary endoscopic system having an illumination system in accordance with the present teachings can include a safety system to prevent excitation laser light from causing accidental damage to tissue. For example, if the small-diameter optical fiber 104 mounted on the outer diameter of the endoscope extrusion experienced breakage, it would be desirable to terminate the transmission of the excitation light to prevent laser exposure (e.g., to the patient). Accordingly, as shown in FIG. 8, an exemplary system is provided in which detection of the reverse fluorescence generated by the phosphors at the distal tip and recaptured by the fiber can be used to terminate transmission of the excitation light (e.g., by de-activating the light source 101). For example, as shown in FIG. 8, the recaptured light, which is transmitted through the fiber 104 in the proximal direction, can be reflected to an optical detector 126 via a short pass filter 123, which allows the short wavelength laser excitation light through with high efficiency, while reflecting the longer wavelength reverse fluorescence. During normal operation, for example, a high amount of long wavelength light would be detected by optical detector 126. However, in a fiber fault situation, the detected signal disappears, and the light source 101 can be de-energized electronically by control 127, or alternatively, a shutter 125 could be activated to prevent continued transmission into the fiber 104.

The section headings used herein are for organizational purposes only and are not to be construed as limiting. While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

What is claimed is:

1. An endoscopic system, comprising:
    an endoscope extending along a central longitudinal axis from a proximal end of the endoscope configured to be disposed external to a patient to a distal end of the endoscope configured to be disposed adjacent a target site within the patient, and
    an optical fiber for delivering excitation light to the distal end of the endoscope and for directing the excitation light radially inward toward the central longitudinal axis,
    wherein said distal end of the endoscope comprises a polymeric tip having one or more phosphors disposed therein for emitting light from the distal tip toward the target site after being stimulated by the excitation light; and
    wherein the optical fiber extends along a fiber longitudinal axis of the optical fiber from the proximal end of the endoscope to the polymeric tip along an external circumferential surface of the endoscope, and wherein a distal portion of the optical fiber is bent radially inward toward the central longitudinal axis.

2. The endoscopic system of claim 1, wherein said one or more phosphors are off-axis.

3. The endoscopic system of claim 2, wherein the central longitudinal axis of the endoscope and the fiber longitudinal axis of the optical fiber are substantially parallel.

4. The endoscopic system of claim 2, wherein said one or more phosphors extend beyond a perimeter of the optical fiber.

5. The endoscopic system of claim 1, wherein the polymer substantially encompasses the distal end of the endoscope, and wherein the one or more phosphors are dispersed throughout the polymer.

6. The endoscopic system of claim 1, further comprising an internal lumen through which a visualization bundle is configured to extend; and
    further comprising a working channel through which one or more instruments can be delivered to the target site.

7. The endoscopic system of claim 6, wherein the internal lumen and the working channel extend through the polymeric tip, and wherein said one or more phosphors are dispersed in said polymer in a space between the internal lumen and the working channel.

8. The endoscopic system of claim 6, wherein the internal lumen and the working channel extend through the polymeric tip, and wherein said one or more phosphors are dispersed in said polymer surrounding the internal lumen and the working channel.

9. The endoscopic system of claim 1, wherein the endoscope is formed through an extrusion process such that the extruded endoscope comprises only two channels extending along the length thereof;
    wherein the endoscope is extruded from reflective material; and
    wherein the optical fiber is disposed external to the extruded endoscope.

10. The endoscopic system of claim 9, wherein the optical fiber terminates in a distal end disposed within or adjacent to the polymeric tip.

11. The endoscopic system of claim 9, wherein light is directed radially inward from a terminal distal end of the optical fiber into the polymeric tip.

12. The endoscopic system of claim 1, wherein said excitation light is in the blue portion of the spectrum; and
    wherein said excitation light comprises substantially coherent light having a wavelength of about 445 nm.

13. The endoscopic system of claim 1, wherein said excitation light is in the violet portion of the spectrum; and
    wherein said excitation light comprises substantially coherent light having a wavelength of about 405 nm.

14. The endoscopic system of claim 1, wherein said distal tip is configured to emit substantially white light in response to receiving said excitation radiation.

15. The endoscopic system of claim 1, wherein flexibility of the endoscopic system is substantially unchanged relative to an endoscopic system lacking the optical fiber.

16. The endoscopic system of claim 1, wherein the optical fiber has a cross-sectional area less than 0.25% of the endoscope.

17. The endoscopic system of claim 1, wherein the optical fiber has a diameter of less than 100 μm.

18. The endoscopic system of claim 1, wherein the polymeric tip comprises a green phosphor and a red phosphor dispersed within the polymer.

19. The endoscopic system of claim 1, wherein the polymeric tip comprises a blue phosphor, a green phosphor, and a red phosphor dispersed within the polymer.

20. The endoscopic system of claim 1, wherein the one or more phosphors are encapsulated within an undoped polymer to prevent contact of the one or more phosphors with the patient.

21. The endoscopic system of claim 1, wherein said light emitted from the distal tip exhibits a CRI greater than 80.

22. The endoscopic system of claim 1, wherein said polymeric tip comprises three phosphors, and wherein said light emitted from the distal tip exhibits a CRI greater than 90.

23. The endoscopic system of claim 1, wherein said polymeric tip comprises four phosphors and the excitation light comprises radiation in the violet portion of the spectrum, and wherein said light emitted from the distal tip exhibits a CRI greater than 95.

24. The endoscopic system of claim 1, further comprising a detector configured to receive light emitted from the one or more phosphors and back-transmitted through the optical fiber toward the proximal end.

25. The endoscopic system of claim 24, further comprising a controller responsive to said detector, wherein the controller is configured to prevent transmission of the excitation light through the optical fiber if back-transmitted light is not detected; and
further comprising a radiation source for generating the excitation light, wherein the controller is configured to deactivate the radiation source if back-transmitted light is not detected.

26. An endoscopic system, comprising:
an endoscope extending along a central longitudinal axis from a proximal end of the endoscope to a distal end of the endoscope, and
an optical fiber for delivering excitation light to the distal end of the endoscope, wherein a distal portion of the optical fiber includes a radially inward bend toward the central longitudinal axis,
wherein said distal end of the endoscope comprises a polymeric tip having one or more phosphors disposed therein for emitting light from the distal tip toward the target site after being stimulated by the excitation light,
wherein a circular reflective band at least partially surrounds a portion of the polymeric tip; and
wherein the optical fiber extends longitudinally along a circumferential surface of the endoscope parallel to the central longitudinal axis and terminates distally at a position radially and longitudinally within the circular reflective band and proximal to the distal end of the endoscope.

27. The endoscopic system of claim 26, wherein the reflective band comprises a metal, a metallized surface, or a reflective polymer, and wherein the reflective band directs light from the optical fiber toward the one or more phosphors and directs light generated by the one or more phosphors toward a visualization target.

28. The endoscopic system of claim 27, wherein a distal-most end of the optical fiber includes a chisel tip to direct light at the distal-most end of the optical fiber toward a radial center of the polymeric tip, and wherein a distal end of the endoscope is reflective.

29. An endoscopic system, comprising:
an endoscope extending along a central longitudinal axis from a proximal end of the endoscope to a distal end of the endoscope, and
an optical fiber for delivering excitation light to the distal end of the endoscope and for directing the excitation light radially inward relative to the central longitudinal axis, wherein the optical fiber includes a fiber longitudinal axis that is parallel to the central longitudinal axis of the endoscope, and wherein the optical fiber includes a distal portion having a radially inward bend toward the central longitudinal axis;
wherein said distal end of the endoscope comprises a polymeric disk having one or more phosphors disposed therein for emitting light from the polymeric disk toward the target site after being stimulated by the excitation light; and
wherein the polymeric disk is positioned within the endoscope proximal to the distal end and is encapsulated within an undoped polymer to prevent contact of the one or more phosphors with the patient.

30. The endoscopic system of claim 29, wherein the polymeric disk extends in a plane parallel to the distal end of the endoscope and perpendicular to the longitudinal axis of the endoscope, and wherein the optical fiber terminates distally in a taper within a proximal portion of the polymeric disk and emits the excitation light to stimulate the one or more phosphors to emit light from the polymeric disk toward the target site.

* * * * *